United States Patent [19]

Klauke et al.

[11] Patent Number: 4,716,229
[45] Date of Patent: Dec. 29, 1987

[54] NEW PYRIMIDINES AND A PROCESS FOR THE PREPARATION OF PYRIMIDINES

[75] Inventors: Erich Klauke, Odenthal; Bernd Baasner; Karl H. Schündehütte, both of Leverkusen, all of Fed. Rep. of Germany

[73] Assignee: Bayer Aktiengesellschaft, Leverkusen, Fed. Rep. of Germany

[21] Appl. No.: 885,041

[22] Filed: Jul. 14, 1986

Related U.S. Application Data

[63] Continuation of Ser. No. 636,458, Jul. 31, 1984, abandoned.

[30] Foreign Application Priority Data

Aug. 4, 1983 [DE] Fed. Rep. of Germany ....... 3328154

[51] Int. Cl.$^4$ ........................................... C07D 239/30
[52] U.S. Cl. .................................................. 544/334
[58] Field of Search ....................................... 544/334

[56] References Cited

U.S. PATENT DOCUMENTS 3,314,955  4/1967  Boudakian et al. ............... 544/334
3,694,444  9/1972  Klauke et al. ...................... 544/334

FOREIGN PATENT DOCUMENTS 0065480  11/1982  European Pat. Off. .
1931640  12/1970  Fed. Rep. of Germany .
1158300   7/1969  United Kingdom .
1273914   5/1972  United Kingdom .

OTHER PUBLICATIONS

Klauke et al., "Chemical Abstracts," vol. 98, 1982, col. 98:89312x.
Banks et al., "Chemical Abstracts," vol. 73, 1970, col. 25402c.
Protsenko, "Chemical Abstracts", vol. 65, 1966, col. 3869f.
Klauke et al., "J. Fluorine Chem.," vol. 21, 1982, pp. 495–513.
Morrison et al., Organic Chemistry, Sec. Ed., 1966, Allyn and Bacon, Inc., Boston, pp. 45–46.
Brown, Herocyclic Compounds, The Pyrimidines, Sup. I, 1970, Wiley–Interscience, New York, pp. 119–122.

Primary Examiner—Glennon H. Hollrah
Assistant Examiner—James H. Turnipseed
Attorney, Agent, or Firm—Sprung Horn Kramer & Woods

[57] ABSTRACT

Pyrimidines substituted in the 5-position by fluorine, some of which are new, are prepared from pyrimidines of the formula

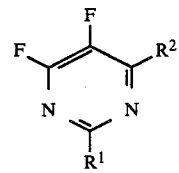

in which
$R^1$ and $R^2$ are identical or different and denote fluorine or trifluoromethyl,
by stepwise reaction with hydrogen chloride.

12 Claims, No Drawings

NEW PYRIMIDINES AND A PROCESS FOR THE PREPARATION OF PYRIMIDINES

This is a continuation of application Ser. No. 636,458, filed July 31, 1984, now abandoned.

The invention relates to pyrimidines, some of which are new, and to a process for their preparation by reacting fluorinated pyrimidines with hydrogen chloride.

2,4,6-Trichloro-5-fluoropyrimidine is known from Ukr. chim. z. 32, (1966), No. 4, 378 to 382.

New pyrimidines of the formula

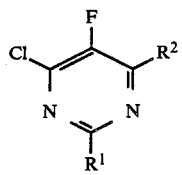

(I)

in which
R$^1$ denotes fluorine or trifluoromethyl, and
R$^2$ denotes fluorine, chlorine or trifluoromethyl, have been found.

The new pyrimidines have biocidal, particularly fungicidal, properties and are used as intermediates for the preparation of carcinostatic and viricidal compounds.

In addition, a process for the preparation of pyrimidines of the formula

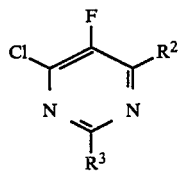

(II)

in which
R$^2$ and R$^3$ are identical or different and denote fluorine, chlorine or trifluoromethyl,
has been found, which process is characterised in that pyrimidines of the formula

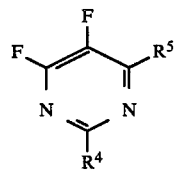

(III)

in which
R$^4$ and R$^5$ are identical or different and denote fluorine or trifluoromethyl,
are reacted with hydrogen chloride under pressure at elevated temperature.

In general, the reaction according to the invention is carried out in the range of pressure 3 to 180 bar.

Using the process, it is likewise possible to prepare the new pyrimidines.

The process according to the invention can be illustrated by the reaction sequence below:

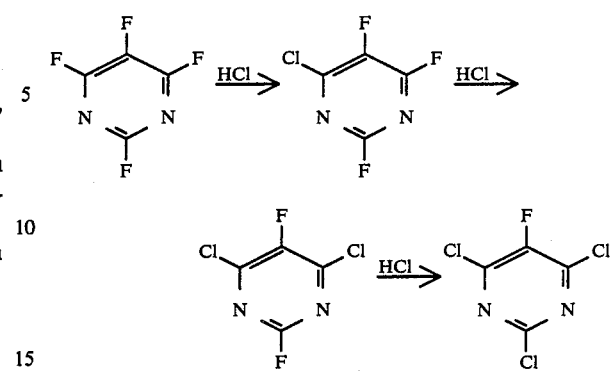

The pyrimidines used as starting compounds are known per se (J. org. Chem. 27, (1962), 2580–2584, J. Chem. Soc. C, (1970), 1280). They can be prepared by, for example, fluorinating, by Cl/F exchange, the corresponding perchlorinated compounds using various fluorinating agents, optionally stepwise (J. Fluorine Chem. 21, (1982) page 495).

In the process according to the invention, the step-wise replacement of the fluorine in the starting pyrimidines by chlorine is preferably carried out by changing the pressure of hydrogen chloride.

Thus, according to the invention, the fluorine substituent in the 6-position of the pyrimidine is replaced by chlorine under a pressure of hydrogen chloride of 3 to 50 bar. This replacement is preferably carried out under a pressure of 5 to 30 bar.

Subsequently, the fluorine substituent in the 4-position of the pyrimidine is replaced by chlorine under a pressure of hydrogen chloride of 12 to 150 bar. This replacement is preferably carried out under a pressure of hydrogen chloride of 15 to 90 bar.

Subsequently, the fluorine substituent in the 2-position of the pyrimidine is replaced by chlorine under a pressure of hydrogen chloride of 50 to 180 bar. This replacement is preferably carried out under a pressure of hydrogen chloride of 55 to 120 bar.

In the case where the 6-, 4- or 2-position is not substituted by fluorine, obviously replacement at this position does not occur, and the replacement takes place in the appropriate sequence.

The process according to the invention is generally carried out in the temperature range from 120° to 250° C., preferably from 150° to 200° C.

The degree of conversion of fluorine into chlorine can very readily be fixed by the parameters of pressure and temperature.

The process according to the invention can be carried out as follows, for example:

The starting compound is initially introduced into an autoclave, and the desired pressure of hydrogen chloride is set up. It is then heated to the reaction temperature according to the invention, it being possible to observe the onset and progress of the reaction by the decrease in the HCl pressure. After reaction is complete, the pressure is released and work-up is preferably by distillation.

The procedure for the process according to the invention is surprising, since aluminum chloride is generally the preferred reagent for the fluorine/chlorine exchange reaction (Houben-Weyl, Vol. V/2, page 493

(1962)), and it could not have been foreseen that hydrogen chloride can be used.

The pyrimidines according to the invention have a strong biocidal effect.

The pyrimidines according to the invention can be reacted in the presence of a hydrogen chloride acceptor and a hydrogenation catalyst to give pyrimidines hydrogenated in the 4- to 6-position.

By alkaline or acidic saponification the corresponding pyrimidinediones (ureides) of the type corresponding to the active compound 5-fluorouracil are obtained.

EXAMPLE 1

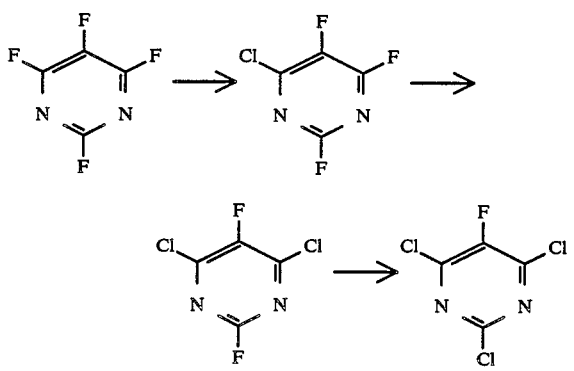

200 g of tetrafluoropyrimidine are initially introduced into a VA stainless steel autoclave, 30 bar of gaseous hydrogen chloride are injected, and the autoclave is heated to 160°. The amount of hydrogen chloride consumed in the reaction is continuously replaced by injection until the pressure remains constant. After 4 hours, the autoclave is cooled, the excess pressure of hydrogen chloride is released and the batch is worked up by distillation. 213 g of crude distillate are obtained, and this, by gas chromatography, has the following composition: 4% starting material, 16% 2,4,5-trifluoro-6-chloropyrimidine, 64% 2,5-difluoro-4,6-dichloropyrimidine and 14.5% 5-fluoro-2,4,6-trichloropyrimidine. The various pyrimidines are isolated by fractional distillation, and the following are obtained:

I. 2,4,5-Trifluoro-6-chloropyrimidine as a liquid of boiling point 121°, $n_D^{20}$: 1.4465
II. 2,5-Difluoro-4,6-dichloropyrimidine as a liquid of boiling point: 162°, $n_D^{20}$: 1.5021
III. 5-Fluoro-2,4,6-trichloropyrimidine boiling point: 82°/14 mbar, melting point: 37°-8°

EXAMPLE 2

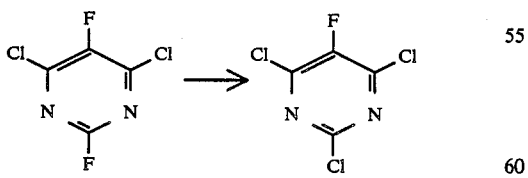

433 g of 2,5-difluoro-4,6-dichloropyrimidine are initially introduced into an autoclave, and are treated with 100 bar of HCl at 200° for 3 h. After cooling and releasing the pressure, 473 g of a mixture of liquid and crystals are obtained, and this, by gas chromatography, has the following composition: 38% 2,5-difluoro-4,6-dichloropyrimidine and 60% 2,4,6-trichloro-5-fluoropyrimidine, which can be readily separated by distillation as described in Example 1.

EXAMPLE 3

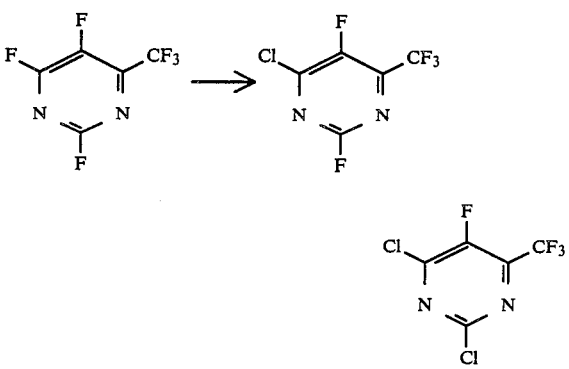

676 g of 2,4,5-trifluoro-6-trifluoromethylpyrimidine are stirred in an autoclave under a HCl pressure of 30 bar and at a temperature of 160° C. for 4 hours. After cooling and releasing the pressure, 785 g of crude product are obtained, and the following are obtained from this by distillation:

465 g of 2,5-difluoro-4-chloro-6-trifluoromethylpyrimidine as a liquid of boiling point: 128°, $n_D^{20}$: 1.4132 and 62 g of 5-fluoro-2,4-dichloro-6-trifluoromethylpyrimidine of boiling point: 157°-9°, $n_D^{20}$: 1.4520.

EXAMPLE 4

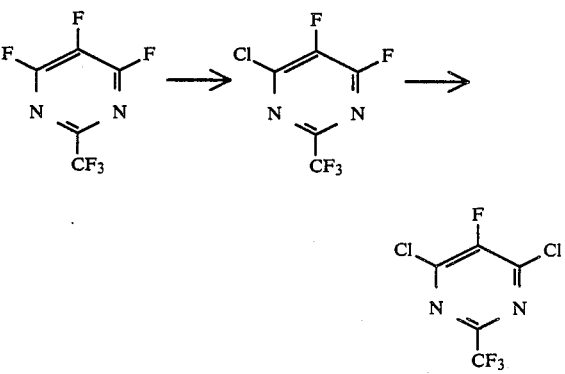

The compounds 2-trifluoromethyl-4,5-difluoro-6-chloropyrimidine, boiling point: 127°, $n_D^{20}$: 1.4091, and 2-trifluoromethyl-4,6-dichloro-5-fluoropyrimidine, boiling point 159°, $n_D^{20}$: 1.4520, can be prepared from 4,5,6-trifluoro-2-trifluoromethylpyrimidine as described in Examples 1 to 3 by treatment at elevated temperature with HCl under pressure.

EXAMPLE 5

Preparation of:

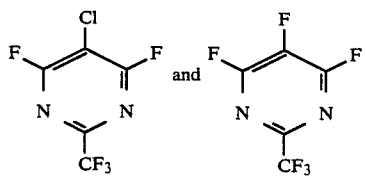

200 g of 4,6-difluoro-5-chloro-2-trichloromethyl-pyrimidine are initially introduced into a 500 ml three-necked flask and, after addition of 135 g of SbF$_3$ and 10 ml of SbCl$_5$, the mixture is slowly heated and stirred at the reflux temperature of 134° for 45 minutes. The batch is cooled, washed with dilute HCl, and the organic constituents are taken up in 300 ml of CH$_2$Cl$_2$ which is dried over MgSO$_4$. 119 g of 2,4-difluoro-5-chloro-2-trifluoromethylpyrimidine, of boiling point 127°, n$_D^{20}$: 1.4095, are obtained from this by distillation.

534 g of the abovementioned compound and 310 g of KF (anhydrous) in 640 ml of tetramethylenesulphone are initially introduced into a stainless steel pressure vessel, and a protective pressure of 3 bar of nitrogen is injected. The mixture is then heated, with vigorous stirring, to 200° and reaction is allowed to continue at this temperature for 4 hours. After cooling, the mixture is distilled from a glass apparatus.

Yield: 449 g of perfluoro(2-methylpyrimidine).
Boiling point: 98°, n$_D^{20}$: 1.3662.

What is claimed is:

1. A pyrimidine of the formula

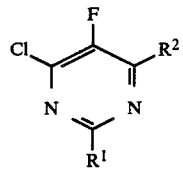

wherein
R$^1$ denotes fluorine or trifluoromethyl, and
R$^2$ denotes fluorine, chlorine or trifluoromethyl.

2. A compound according to claim 1, wherein R$^1$ and R$^2$ both denote fluorine.

3. A compound according to claim 1, wherein at least one of R$^1$ and R$^2$ is trifluoromethyl.

4. A compound according to claim 1, wherein both R$^1$ and R$^2$ are trifluoromethyl.

5. A compound according to claim 1, wherein R$^2$ denotes chlorine.

6. A process for the preparation of a pyrimidine

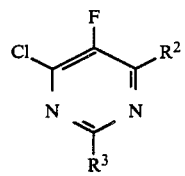

wherein
R$^2$ and R$^3$ are identical or different and denote fluorine, chlorine or trifluoromethyl which comprises contacting a pyrimidine $$\begin{array}{c}\text{F}\\ \text{F} \diagdown \diagup \text{R}^5\\ \text{N} \quad \text{N}\\ \diagdown \diagup\\ \text{R}^4\end{array}$$

wherein
R$^4$ and R$^5$ are identical or different and denote fluorine or trifluoromethyl with hydrogen chloride under pressure at an elevated temperature.

7. A process according to claim 6, wherein the process is carried out at a pressure of 3 to 50 bar and at a temperature of 120° to 250° C.

8. A process according to claim 6, wherein the process is performed at a hydrogen chloride pressure of 3 to 50 bar and the pyrimidine has a fluorine substituent at the 6 position.

9. A process according to claim 6, wherein the pyrimidine has a fluorine substituent in the 4 position and the process is carried out at a hydrogen chloride pressure of 12 to 150 bar.

10. A process according to claim 6, wherein the pyrimidine has a fluorine substituent in the 2 position and the process is carried out under a hydrogen chloride pressure of 50 to 180 bar.

11. A process according to claim 6, wherein the process is carried out at a temperature of 120° to 250° C.

12. A process according to claim 6, wherein the process is carried out in the absence of aluminum chloride.

* * * * *